US005772672A

United States Patent [19]
Toy et al.

[11] Patent Number: 5,772,672
[45] Date of Patent: *Jun. 30, 1998

[54] ENDOSCOPIC SUTURE PASSER

[75] Inventors: Frederick K. Toy; Roy T. Smoot; Robert H. LaPrad, all of Seaford, Del.

[73] Assignee: W.L. Gore & Associates, Inc., Newark, Del.

[ * ] Notice: The term of this patent shall not extend beyond the expiration date of Pat. No. 5,618,290.

[21] Appl. No.: 834,757

[22] Filed: Apr. 3, 1997

Related U.S. Application Data

[60] Division of Ser. No. 377,762, Jan. 24, 1995, Pat. No. 5,618,290, which is a continuation-in-part of Ser. No. 14,349, Oct. 19, 1993, Pat. No. Des. 368,776.

[51] Int. Cl.⁶ .................................................. A61B 17/04
[52] U.S. Cl. ........................ 606/139; 606/144; 606/145
[58] Field of Search ..................... 606/139, 144, 606/145, 146, 148, 151, 232

[56] References Cited

U.S. PATENT DOCUMENTS

| | | | |
|---|---|---|---|
| D. 368,776 | 4/1996 | Toy et al. ............................... | D24/145 |
| 2,268,755 | 1/1942 | Li . | |
| 3,088,454 | 5/1963 | Shute ......................................... | 128/2 |
| 3,831,202 | 8/1974 | Hulsen ........................................ | 3/1 |
| 3,831,585 | 8/1974 | Brondy et al. ............................. | 128/2 |
| 3,857,395 | 12/1974 | Johnson et al. . | |
| 3,998,230 | 12/1976 | Miller . | |
| 4,235,238 | 11/1980 | Ogiu et al. . | |
| 4,378,019 | 3/1983 | Yamada . | |
| 4,660,570 | 4/1987 | Dombrowski . | |
| 4,928,669 | 5/1990 | Sullivan . | |
| 4,952,207 | 8/1990 | Lemieux ................................. | 604/164 |
| 4,994,079 | 2/1991 | Genese et al. ......................... | 606/206 |
| 5,100,415 | 3/1992 | Hayhurst ................................ | 606/139 |
| 5,147,379 | 9/1992 | Sabbaghian et al. ................... | 606/206 |
| 5,181,919 | 1/1993 | Bergman et al. ....................... | 606/144 |
| 5,281,237 | 1/1994 | Gimpelson ............................. | 606/144 |
| 5,290,297 | 3/1994 | Phillips ................................... | 606/144 |
| 5,304,187 | 4/1994 | Green et al. ............................ | 606/151 |
| 5,320,629 | 6/1994 | Noda et al. ............................. | 606/139 |
| 5,480,405 | 1/1996 | Yoon ....................................... | 606/139 |
| 5,501,692 | 3/1996 | Riza ........................................ | 606/148 |

*Primary Examiner*—Gary Jackson
*Attorney, Agent, or Firm*—Dann, Dorfman, Herrell and Skillman, P.C.; Henry H. Skillman

[57] ABSTRACT

An endoscopic suturing device is provided for manipulating a suture to form a stitch through a tissue within a body cavity. The suturing device comprises a needle with a shaft, a pointed end located at the distal end of the suturing device, a receptacle formed proximally to the pointed end, and a latch for opening and closing the receptacle. The latch is biased to the open position. A tubular sheath is provided which is concentric with the needle shaft, the needle shaft being frictionally slidable within the tubular shaft. The suture is clamped by the device by inserting the suture into the receptacle and sliding the tubular sheath over the latch, thereby closing the receptacle. The suture can then be released by sliding the tubular sheath to uncover the latch, thereby opening the receptacle.

12 Claims, 2 Drawing Sheets

ENDOSCOPIC SUTURE PASSER

RELATED APPLICATION

This application is a division of our application Ser. No. 08/377,762, now U.S. Pat. No. 5,618,290, which is continuation-in-part of our Design patent application Ser. No. 29/014,349, filed Oct. 19, 1993, now U.S. Design Pat. No. D-368,776.

FIELD OF THE INVENTION

The present invention relates to an endoscopic suturing device for securing tissue within a body cavity using sutures.

BACKGROUND OF THE INVENTION

Endoscopic surgical techniques have been used successfully to perform a variety of surgical procedures including vagotomies, appendectomies, laparotomies, gall-bladder removals, lysis of adhesions from scar tissue, and hernia repairs, in addition to many other operations.

The use of endoscopic surgical procedures can provide benefits over conventional surgical techniques to both the surgeon and the patient. The time required to perform endoscopic surgery is often significantly less than the time required to perform the same operation using conventional surgical techniques. In addition, endoscopic procedures decrease the amount of pain and discomfort suffered by the patient while also decreasing the recovery time and the amount of scarring.

However, endoscopic surgical procedures are hampered because such procedures require the use of specialized tools in order to effectively work in an endoscopic surgical environment. Since only a small incision is made in the patient, the surgeon's access to the operating site is restricted. Therefore, new instruments are needed when working in an endoscopic environment.

Devices for endoscopically closing hernia defects have been developed and can be broadly classified as either stapling or suturing devices. Although sutures are cheaper and less likely to cause adverse reactions, current suturing devices suffer in that they do not securely clamp the suture and the suture is difficult to mount within the device. Furthermore, existing devices make it difficult to place the sutures in the operating site at the optimal locations for suture passing and tying. As a result, endoscopic suturing techniques generally require longer operating times than do stapling techniques.

U.S. Pat. No. 4,923,461 relates to a method for arthroscopic suturing of tissue within the body without requiring open surgery. The method involves penetrating the tissue to be sutured with a hollow needle and feeding the suture material through the hollow needle. The needle is then removed and the suture knotted. However, this method has the disadvantage of having to clamp onto the suture end and withdraw it from the body in order to knot the suture. In addition, this method cannot be used to provide a running seam. Further, the device necessary to perform such a procedure is bulky and, therefore, restrictive in use.

Accordingly, it would be highly desirable to have an endoscopic suturing device that is easy to use, easy to manipulate, and securely clamp the suture, and wherein the suture is easily mounted within the suture passer. In use, the suturing device should enable placement of the sutures at optimum locations in the operating site and desirably enable tying of the sutures subcutaneously.

SUMMARY OF THE INVENTION

In accordance with the present invention, an endoscopic suturing device is provided for suturing tissue within a body cavity during endoscopic surgical procedures. The device is easy to use, easy to manipulate, and securely clamps the suture. Additionally, the suture is easily mounted within the suturing device.

The device comprises a suture passer having a pointed distal end adapted to be inserted through the skin into the body cavity. An open receptacle is provided proximally to the pointed end. A latch, which is spring-biased to the open position, is provided for opening and closing the receptacle. A tubular sheath is provided which is concentric with the needle, the needle being frictionally slidable within the tubular sheath, so that the receptacle is open when the latch is extended from the tubular sheath and the receptacle is closed when the latch is retracted within the tubular sheath.

BRIEF DESCRIPTION OF THE DRAWINGS

The foregoing summary, as well as the following detailed description of the preferred embodiments of the present invention, will be better understood when read in conjunction with the accompanying drawings, in which.

DETAILED DESCRIPTION OF THE INVENTION

Figure 1:
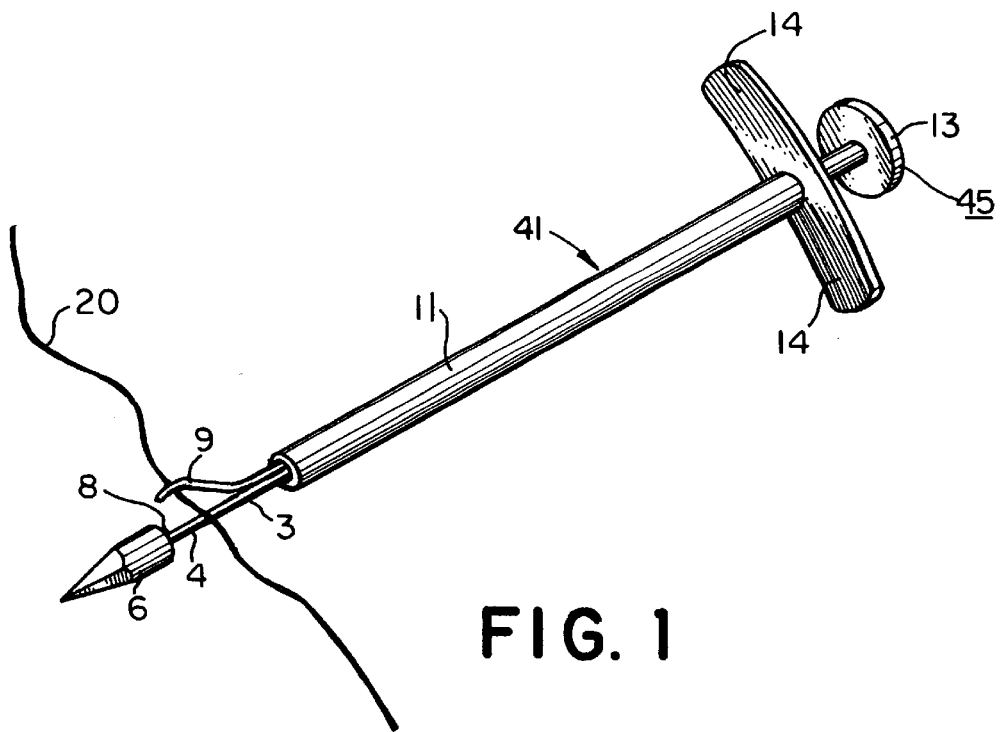
FIG. 1 is a perspective view of a first embodiment of a suture passer embodying the present invention for manipulating a suture to form a stitch in a tissue within a body cavity.
Figure 2:
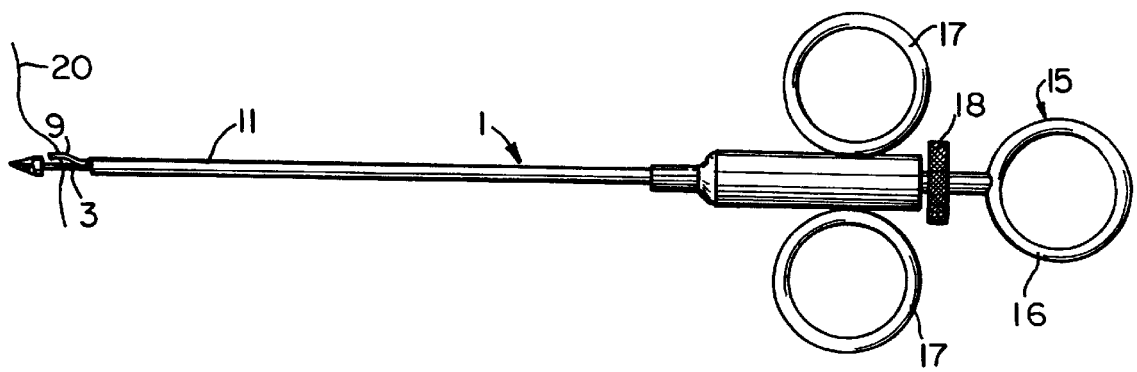
FIG. 2 is a front elevational view of a second and preferred embodiment of a suture passer embodying the present invention with the receptacle in the open position.
Figure 3:
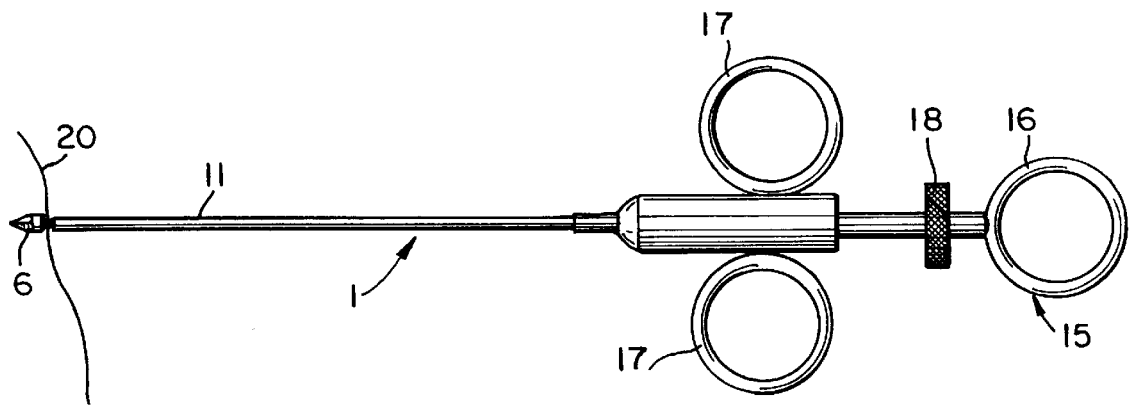
FIG. 3 is a front elevational view of the device in the closed position.
Figure 4:
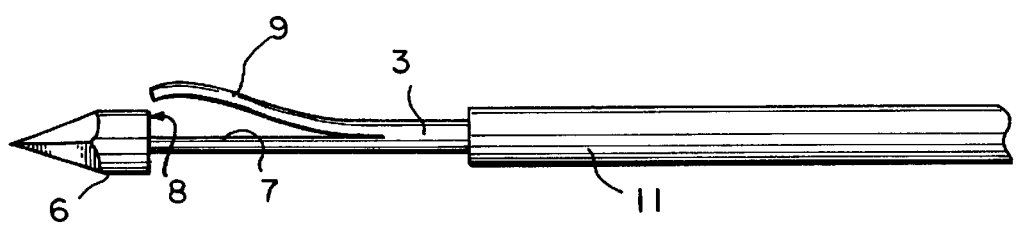
FIG. 4 is an enlarged fragmentary front elevational view of the distal end of the suturing device with the receptacle in the open position.
Figure 5:
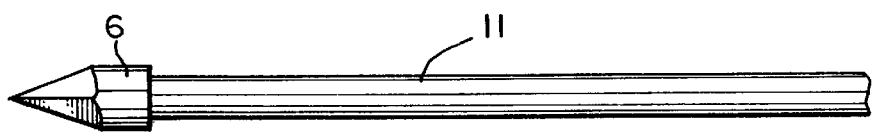
FIG. 5 is a view similar to FIG. 4 with the receptacle in the closed position.

FIGS. 1 through 3 show two forms of endoscopic suturing device, generally designated 41 and 1 respectively, for endoscopically suturing tissue within a body cavity. Each suturing device comprises a needle shaft 3. An enlarged pointed head 6 at the distal end 4 of the needle shaft 3 provides a pointed distal end for the suturing device. The underside of the pointed head 6 at its junction with the shaft 3 forms a shoulder which provides an open receptacle 8 extending along the needle shaft 3 from the distal end towards the proximal end, terminating at a location spaced from the distal end. A latch 9, which is spring-biased to the open position, is provided for opening and closing the receptacle 8. The latch 9 is anchored at one end at the proximal end of the receptacle and extends along the receptacle, terminating in a free end at the distal end of the receptacle 8 needle shaft 3. A tubular sheath 11 surrounds and is concentric with the needle shaft 3 and is dimensioned so that the needle shaft 3 is frictionally slidable within the tubular sheath 11. The receptacle 8 can be opened by extending the needle shaft 3 to space its head 6 from the distal end of the tubular sheath 11 beyond the proximal end of the receptacle as shown in FIG. 2, and the receptacle 8 can be closed by retracting the needle shaft 3 to withdraw the latch 9 within the tubular sheath 11, causing the latch to close the distal end of the receptacle. In this manner, a suture 20 can be selectively captured by or released from the suturing device 1. A handle 45 is provided at the proximal end of the suture passer 41, and a different handle 15 is provided at the proximal end of the suture passer 1.

Each of the handles includes a grip on the shaft 3 and a cooperating grip on the sheath 11. In the passer 41 of FIG. 1, the shaft grip is in the form of a plunger thumb rest 13, and the sheath grip is in the form of a pair of finger rests 14,14, similar to the grip portion of a hypodermic needle. In the suture passer 1 of FIG. 2, the shaft grip comprises a thumb loop 16 and the sheath grip comprises finger loops 17 to extend the latch 9 relative the tubular sheath 11. Either handle 45 or 15 aids in manipulating the suturing device 41 or 1.

In each embodiment, the sliding engagement of the shaft in the sheath not only permits relative axial displacement, but also affords relative rotational displacement of the shaft within the sheath. It is preferred to provide rotation of the shaft 3 within the sheath to vary the presentation of the receptacle and facilitate manipulation of the suture when it is engaged in the receptacle without having to rotate the sheath when it is placed into the body cavity. In the embodiment of FIG. 1, the thumb plunger 13 may be rotated to rotate the shaft 3 within the sheath, and in the embodiment of FIG. 2, a thumb wheel 18 is provided to serve as a rotator for the shaft 3. Rotation of the shaft 3 at the proximal end of the suture passer affords rotation of the receptacle 8 at the distal end of the suture passer.

In the present instance, the latch 9 comprises a flexible leaf which is formed integrally with the shaft by a longitudinal cut 7 extending from the head 6 a short distance towards the proximal end. The cut 7 leaves a cutaway portion of shaft 3 which produces the receptacle 8. The free end of the leaf 9 produced by the cut 7 is severed from the shaft 3 and is biased to a position in which it curves outwardly from the cut to provide a separation between the free end of the leaf 9 and the distal end of the receptacle 8. In this position, the leaf opens the receptacle to allow capture of a suture between the leaf 9 and the body of the shaft 3. The flexibility of the leaf allows the free end of the leaf to close the receptacle, for example when the shaft 3 is withdrawn into the interior of the sheath 11. The receptacle 8, in the present instance, is formed at the junction of the cut 7 with the underside of the enlarged head 6.

It is noted that in the illustrated embodiments, the needle shaft 3 is of lesser diameter than the head 6 so that a shoulder is formed at the underside of the head 6 at its junction with the shaft 3. As shown, the sheath 11 is tubular in form with an interior diameter adapted to frictionally and slidably receive the shaft 3 and an outer diameter which is slightly less than the outer diameter of the head 6. Thus, when the shaft 3 is withdrawn into the sheath 11, the sheath flexes the leaf 9 against the cut 7 and allows the distal end of the sheath 11 to engage against the shoulder formed at the underside of the head 6. If a suture is captured within the receptacle 8, the longitudinal displacement of the sheath relative to the head 8 not only captures the suture within the receptacle, but also clamps the suture between the end of the sheath 11 and the underside of the head 6. In accordance with the invention, the flexible leaf 9 is biased outwardly from the cut 7 so that the receptacle 8 is normally open.

Preferably, the needle shaft 3 is constructed from a spring material and is heat treated to provide a spring bias for the latch 9. In addition, the shaft 3, the pointed head 6, the receptacle 8, the latch 9 and the sheath 11 are preferably fabricated from heat-resistant material so as to withstand sterilizing temperatures without degradation of the spring bias or the frictional sliding of the shaft 3 within the sheath 11.

It will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

We claim:

1. A suturing device having a proximal end with a handle and a pointed distal end, comprising:

a needle having a shaft;

a suture-receiving receptacle on said shaft proximal to said pointed distal end; and a latch on said shaft displaceable between open and closed positions for opening and closing said receptacle, said latch being spring-biased to the open position;

said handle comprising means for operating said latch.

2. The device as recited in claim 1 wherein the means for operating said latch comprises a tubular sheath concentric with said needle shaft and extending between said proximal end and said latch, said needle shaft being frictionally slidable within said tubular sheath, said latch being displaced by said spring bias to open said receptacle when said needle shaft is extended relative to said tubular sheath and said latch being displaced by said sheath to close said receptacle when said needle shaft is retracted relative to said tubular sheath.

3. The device as recited in claim 2 wherein said handle has one grip connected to said needle shaft at its proximal end and a second grip connected to the sheath at its proximal end for extending and retracting said receptacle relative to the distal end of said tubular sheath.

4. The device as recited in claim 3 further comprising a rotator attached to said shaft at its proximal end for rotating the shaft of said suturing device within said sheath, and rotating said receptacle at the distal end of the device.

5. The device as recited in claim 3 wherein said one grip comprises a thumb rest and said second grip comprises a pair of finger rests.

6. The device as recited in claim 3 wherein said one grip comprises a thumb loop and said second grip comprises a pair of finger loops.

7. The device as recited in claim 1 wherein the distal end of said shaft terminates in a head larger than said needle shaft to provide a shoulder intermediate said shaft and said head, said shaft and shoulder forming said receptacle.

8. The device as recited in claim 7 wherein the means for operating said latch comprises a tubular sheath concentric with said needle shaft and extending between said proximal end and said receptacle, and having an outer dimension at its distal end not substantially larger than said head, said needle shaft being frictionally slidable within said tubular sheath, said latch being displaced by said spring bias to open said receptacle when said needle shaft is extended relative to said tubular sheath and said latch being displaced by said sheath to close said receptacle when said needle shaft is retracted relative to said tubular sheath.

9. The device as recited in claim 8 wherein said handle has one grip connected to said needle shaft at its proximal end and a second grip connected to the sheath at its proximal end for extending and retracting said receptacle relative to the distal end of said tubular sheath.

10. The device as recited in claim 9 further comprising a rotator attached to said shaft at its proximal end for rotating the shaft of said suturing device within said sheath, and rotating said receptacle at the distal end of the device.

11. A suturing device having a proximal end with a handle and a pointed distal end, comprising:

a needle having a shaft;

a suture-receiving receptacle in said shaft proximal to said pointed distal end;

said receptacle having a distal end adjacent the distal end of the shaft and extending along said shaft from its distal end toward said proximal end of the device, said receptacle terminating in a proximal end spaced a distance from its distal end, and a latch on said shaft coextensive with said receptacle, said latch having one end anchored to said shaft at the proximal end of the receptacle and having a free end adjacent the distal end of the receptacle, said free end being displaceable between open and closed positions for opening and closing said receptacle, said latch being spring-biased to the open position;

said handle comprising means for operating said latch.

12. A suturing device according to claim 11, wherein said receptacle comprises a cutaway portion of said needle shaft.

* * * * *